United States Patent [19]

Exner et al.

[11] Patent Number: 5,866,182
[45] Date of Patent: Feb. 2, 1999

[54] PRESERVATIVE, METHOD OF USE THEREOF TO PRESERVE DRINKS AND DRINKS PRESERVED THEREBY

[75] Inventors: Otto Exner, Ratingen; Martin Kugler, Leichlingen; Manfred Hoffmann, Tönisvorst, all of Germany

[73] Assignee: Bayer Aktiengesellschaft, Leverkusen, Germany

[21] Appl. No.: 817,017
[22] PCT Filed: Sep. 13, 1995
[86] PCT No.: PCT/EP95/03599
 § 371 Date: Mar. 19, 1997
 § 102(e) Date: Mar. 19, 1997
[87] PCT Pub. No.: WO96/09774
 PCT Pub. Date: Apr. 4, 1996

[30] Foreign Application Priority Data

Sep. 26, 1994 [DE] Germany ............ 44 34 314.0

[51] Int. Cl.⁶ .............. A23B 7/10; A23B 7/157; A23L 2/44
[52] U.S. Cl. ........ 426/330.3; 426/321; 426/532; 426/597; 426/590; 426/599; 426/654
[58] Field of Search ............... 426/321, 532, 426/597, 599, 590, 654, 330.3

[56] References Cited

U.S. PATENT DOCUMENTS 3,936,269  2/1976  Bayne .
3,979,524  9/1976  Bayne .
5,021,251  6/1991  Kenna, et al. .

FOREIGN PATENT DOCUMENTS 604217   12/1990  Australia .
731582   10/1969  Belgium .
1140802  12/1962  Germany .
355019    7/1961  Switzerland .

OTHER PUBLICATIONS

Barth et al. Preservation of dealcoholised wine with preservatives, Der Deutsche Weinbau, Wiesbaden, (1991) 461229–1236, 1991.

Food Technology, vol. 20, No. 10, Oct. 1966, Chicago, US, pp. 120–122, W.O. Harrington, et al. "Preservative effects of diethyl . . . cider".

*Primary Examiner*—Helen Pratt
*Attorney, Agent, or Firm*—Sprung Kramer Schaefer & Briscoe

[57] ABSTRACT

A drink preservative for sterilizing drinks containing:

a) K-sorbate and/or Na-benzoate;

b) ascorbic acid; and c) dimethyl dicarbonate;

a method for sterilizing and preserving drinks by incorporating the drink preservative into drinks; and drinks preserved with the drink preservative.

11 Claims, No Drawings

PRESERVATIVE, METHOD OF USE THEREOF TO PRESERVE DRINKS AND DRINKS PRESERVED THEREBY

The application relates to a dimethyl dicarbonate/potassium sorbate/ascorbic acid combination for sterilizing non-carbonated and carbonated beverages.

Soft drinks based on fruit juice, instant tea drinks, many other soft drinks of individual types, wine coolers, but also de-alcoholized wines and other wines must generally be protected against infection/spoilage by moulds, yeasts and bacteria. Many methods are known, such as, for example, aseptic packaging, hot-filling, tunnel pasteurization and use of persistent preservatives. The use of dimethyl dicarbonate (e.g. Velcorin®) known as cold sterilization has also been gaining ever greater importance for many products which are difficult to preserve. However, those skilled in the art are still currently confronted with particularly difficult problem cases. In particular, in the case of the non-carbonated, still soft drinks, drinks based on fruit juice and/or based on tea, even when known preservation methods are used, problems can occur, such as resistance phenomena when salts of sorbic and benzoic acids are used, off-taste in the event of overdosing use restricted by national legislation, the maximum permitted dose not always being sufficient in this case.

The increased usage of reusable packages made of plastic, in particular the PET bottle, which, as is of course known, cannot as a rule be used for preservation by means of pasteurization, has also drastically increased the requirement for efficient preservation methods without heat treatment. It is also known that owing to the use of many a sweetener combination, for flavour and stability reasons, the pH of the soft drink has been markedly increased to approximately 4. At this relatively high pH, the concentration of the organic acids which are used as preservatives in the form of the salts-sorbic acid, benzoic acid or potassium sorbate or sodium sorbate and sodium benzoate-must likewise be increased, since the antimicrobial action of these acids is greatly pH-dependent and only the undissociated form is active.

It is further known that the water hardness greatly influences the antimicrobial activity, e.g. of potassium sorbate. In this case, as a result of the increased $CaCO_3/MgCO_3$ content, the formation of calcium sorbate, for example, occurs, which readily flocculates out and then no longer contributes to the preservation of the drink. In order to compensate for this effect, markedly higher potassium sorbate concentrations must as a rule be used for preservation of the drinks, which leads to an impairment of the taste of the drink or, in accordance with the particular national legislation, in some circumstances is not permitted in these concentrations. For these cases, in practice, high capital expenditure must be effected to decrease the carbonate hardness.

It has now surprisingly been found that by means of a combined use of ascorbic acid, K-sorbate and/or Na-benzoate, and dimethyl dicarbonate (DMDC), an outstanding preservation of drinks is achieved even at high water hardness (expressed as $CaCO_3$ content).

Thus, for example, 175 or 230 ppm of DMDC in combination with 300 ppm of K-sorbate and 240 ppm of ascorbic acid are able to preserve drinks effectively at high water hardness, (equivalent to 300 ppm of $CaCO_3$).

Drinks are taken to mean here preferably soft drinks, such as non-alcoholized, flavoured soft drinks, such as lemonades, fruit juice-containing soft drinks, tea (so-called ready-to-drink tea drinks) mixed drinks of a tea/fruit juice-containing soft drink, but also corresponding concentrates and wine coolers and dealcoholized wines.

Wines within the meaning of diverse national legislations may also, to the extent that the legislation permits this, be reliably preserved with the combination according to the invention with greatly reduced $SO_2$ content. The combination according to the invention will primarily be used in still drinks of the abovementioned listing, but slightly carbonated drinks and also carbonated drinks can also be advantageously sterilized with this combination according to the invention. Preferably, the combination according to the invention is used in so-called still, i.e. non-carbonated tea drinks and tea/mixed drinks.

Preference is given in the context of the invention to the conjoint use of 50 to 250 ppm of dimethyl dicarbonate, in total 200 to 500 ppm of K-sorbate and/or Na-benzoate and 100 to 500 ppm of ascorbic acid for the preservation of abovementioned drinks, the degree of hardness of the water used not impairing the conservation quality.

Particular preference is given in the context of this invention to the use of 150 to 250 ppm of dimethyl dicarbonate, 250 to 350 ppm of K-sorbate and 150 to 400 ppm of ascorbic acid, in particular for the preservation of drinks having a particularly high water hardness.

The drinks are produced by conventional processes, preferably, the individual drink constituents being mixed with K-sorbate and/or Na-benzoate and ascorbic acid and then being admixed with dimethyl dicarbonate by means of a suitable metering apparatus, in particular metering units such as LEWA DA9 or corresponding Burdomat types.

EXAMPLE

1. A non-carbonated tea/water mixture (tea drink) having a water hardness of 300 ppm of $CaCO_3$ content is admixed with 175 ppm of Velcorin®, 300 ppm of K-sorbate and 240 ppm of ascorbic acid. The drink obtained is adequately and persistently preserved.

2. 230 ppm of Velcorin® are added analogously to Example 1. In this case also, an adequately and persistently preserved tea drink is obtained.

We claim:

1. A preservative for sterilizing drinks comprising a preservative effective amount of:
   a) K-sorbate and/or Na-benzoate;
   b) ascorbic add; and
   c) dimethyl dicarbonate.

2. A method for sterilizing and preserving a drink comprising incorporating into said drink a preservative effective amount of a preservative comprising:
   a) K-sorbate and/or Na-benzoate;
   b) ascorbic acid; and
   c) dimethyl dicarbonate.

3. The method according to claim 2, wherein said preservative comprises:
   a) 200 to 500 ppm of K-sorbate and/or Na-benzoate;
   b) 100 to 500 ppm of ascorbic acid; and
   c) 50 to 250 ppm of dimethyl dicarbonate.

4. The method according to claim 2, wherein said preservative comprises:
   a) 250 to 350 ppm of K-sorbate and/or Na-benzoate;
   b) 150 to 400 ppm of ascorbic acid; and
   c) 150 to 250 ppm of dimethyl dicarbonate.

5. The method according to claim 2, wherein said drink has a water hardness equivalent to 300 ppm $CaCO_3$.

6. The method according to claim 2, wherein said drink is a still, noncarbonated soft drink.

7. The method according to claim 2, wherein said drink is a tea or tea/fruit juice mixture.

8. A drink comprising a preservative effective amount of a preservative according to claim 1.

9. The drink according to claim 8, which has a water hardness equivalent to 300 ppm $CaCO_3$.

10. The drink according to claim 8, which is a still, noncarbonated soft drink.

11. The drink according to claim 8, is a tea or tea/fruit juice mixture.

* * * * *